United States Patent
Kang et al.

(10) Patent No.: US 10,443,040 B2
(45) Date of Patent: Oct. 15, 2019

(54) METHOD FOR PREPARING ANTIGEN-SPECIFIC CYTOTOXIC T-CELLS BY USING ACTIVATED B-CELLS AND USE THEREOF

(71) Applicant: SEOUL NATIONAL UNIVERSITY R&DB FOUNDATION, Seoul (KR)

(72) Inventors: Hyoung Jin Kang, Seoul (KR); Sun Ok Yun, Seoul (KR); Chang-Yuil Kang, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 24 days.

(21) Appl. No.: 15/720,508

(22) Filed: Sep. 29, 2017

(65) Prior Publication Data

US 2018/0023054 A1 Jan. 25, 2018

Related U.S. Application Data

(63) Continuation-in-part of application No. PCT/KR2015/005075, filed on May 21, 2015.

(30) Foreign Application Priority Data

Mar. 31, 2015 (KR) ........................ 10-2015-0045476

(51) Int. Cl.
*C12N 5/0783* (2010.01)
*A61K 35/17* (2015.01)
*A61K 39/00* (2006.01)
*A61K 39/235* (2006.01)
*A61K 39/245* (2006.01)

(52) U.S. Cl.
CPC ........ *C12N 5/0638* (2013.01); *A61K 39/0011* (2013.01); *A61K 39/235* (2013.01); *A61K 39/245* (2013.01); *A61K 2039/5158* (2013.01); *C12N 2710/10034* (2013.01); *C12N 2710/16134* (2013.01); *C12N 2710/16234* (2013.01)

(58) Field of Classification Search
None
See application file for complete search history.

(56) References Cited

U.S. PATENT DOCUMENTS

2010/0028380 A1* 2/2010 Kang .................... A61K 39/00
424/204.1

OTHER PUBLICATIONS

Kim 2008 (Int J Cancer.122:2774-2783) (Year: 2008).*
Van den Bosch (Clin Exp Immunol. 2005;139(3):458-467) (Year: 2005).*
Chung et al., . Cancer Res. 2006;66:6843-6850. (Year: 2006).*
Chen et al., Immunobiology 218:1477-1487 (Year: 2013).*
Kim et al., Cellular Immunology 270:135-144 (Year: 2011).*
Kang et al., "Successful Engraftment with Fludarabine, Cyclophosphamide, and Thymoglobulin Conditioning Regimen in Unrelated Transplantation for Severe Aplastic Anemia: A Phase II Prospective Multicenter Study", Biol Blood Marrow Transplant, vol. 16, pp. 1582-1588, (2010).
Peck et al., "Respiratory virus infection among hematopoietic cell transplant recipients: evidence for asymptomatic parainfluenza virus infection", Blood, vol. 110, pp. 1681-1688, (2007).
Papadopoulos et al., "Infusions of Donor Leukocytes to Treat Epstein-Barr Virus-Associated Lymphoproliferative Disorders After Allogeneic Bone Marrow Transplantation", N Engl J Med, vol. 330, pp. 1185-1191, (1994).
Fischer, "Emerging Viruses in Transplantation: There is More to Infection After Transplant Than CMV and EBV", Transplantation, vol. 86, pp. 1327-1339, (2008).
Erard et al., "Emerging viral infections after hematopoietic cell transplantation", Pediatr Transplantation, vol. 9, Suppl. 7, pp. 48-54, (2005).
Kang et al., "Double umbilical cord blood transplantation for children and adolescents", Ann Hematol, vol. 89, pp. 1035-1044, (2010).
Leen et al., "Cytotoxic T lymphocytes as immune-therapy in haematological practice", Br J Haematol, vol. 143, No. 2, pp. 169-179, (2008).
Leen et al., "Challenges of T cell therapies for virus-associated diseases after hematopoietic stem cell transplantation", Expert Opinion on Biological Therapy, vol. 10, No. 3, pp. 337-351, (2010).
Zerr et al., "Clinical Outcomes of Human Herpesvirus 6 Reactivation after Hematopoietic Stem Cell Transplantation", CID, vol. 40, pp. 932-940, (2005).
Rosenberg et al., "Adoptive cell transfer: a clinical path to effective cancer immunotherapy", Nature Reviews—Cancer, vol. 8, pp. 299-308, (2008).
Bruno et al., "Adenovirus Infection in Hematopoietic Stem Cell Transplantation: Effect of Ganciclovir and Impact on Survival", Biology of Blood and Marrow Transplantation, vol. 9, pp. 341-352, (2003).
Leen et al., "Adenovirus as an emerging pathogen in immunocompromised patients", British Journal of Haematology, vol. 128, pp. 135-144, (2004).

* cited by examiner

*Primary Examiner* — Daniel C Gamett
(74) *Attorney, Agent, or Firm* — Vorys, Sater, Seymour & Pease LLP; Mih Suhn Koh

(57) ABSTRACT

Disclosed in the present application are: a method for preparing in vitro/ex vivo antigen-specific cytotoxic T-cells by using B cells treated with biological response modifier; and a use thereof. The cytotoxic T-cells prepared by the method of the present application can be used advantageously for treating infectious disease and cancer and the like.

14 Claims, 9 Drawing Sheets

[Fig. 1]
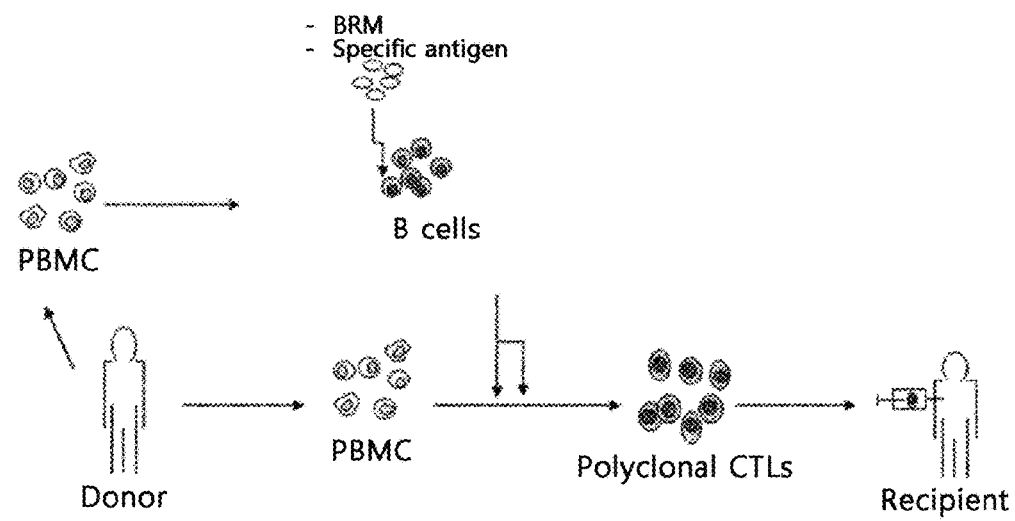
[Fig. 2]
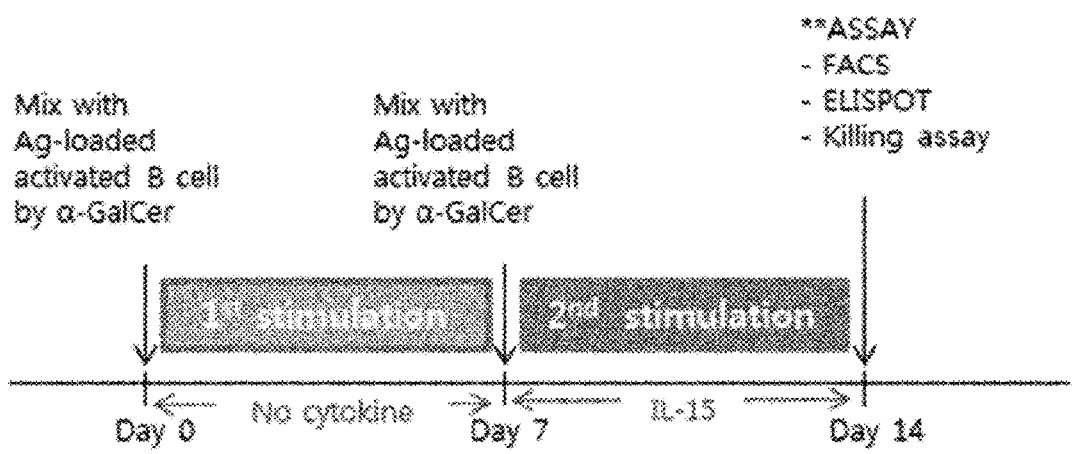

[Fig. 3A]
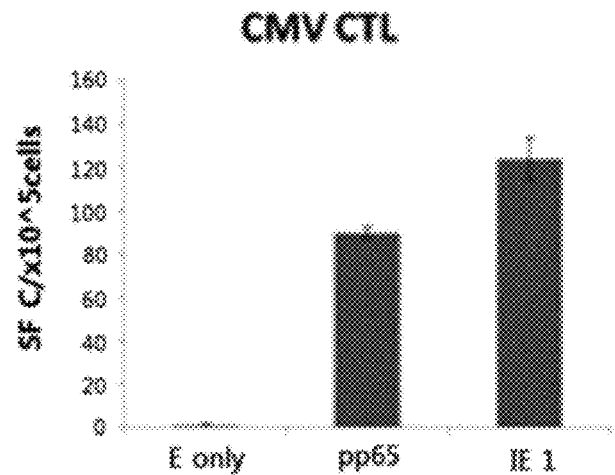
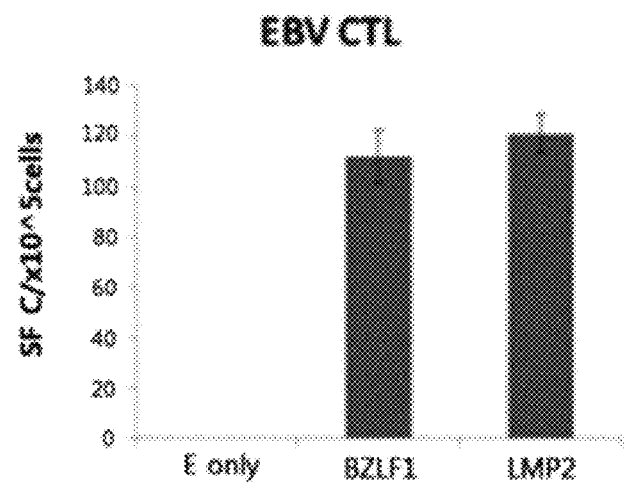
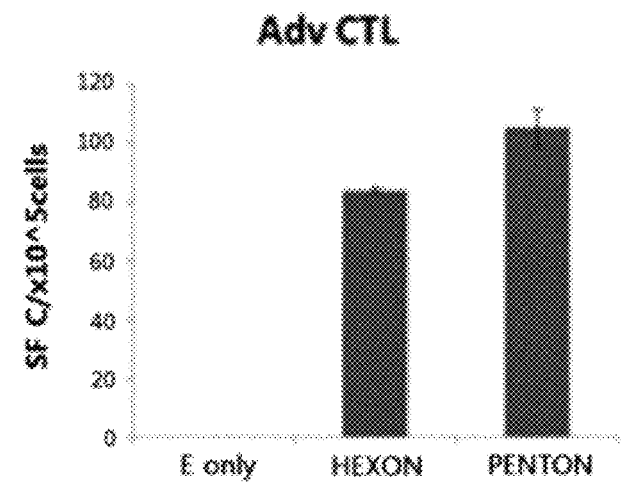

[Fig. 3B]
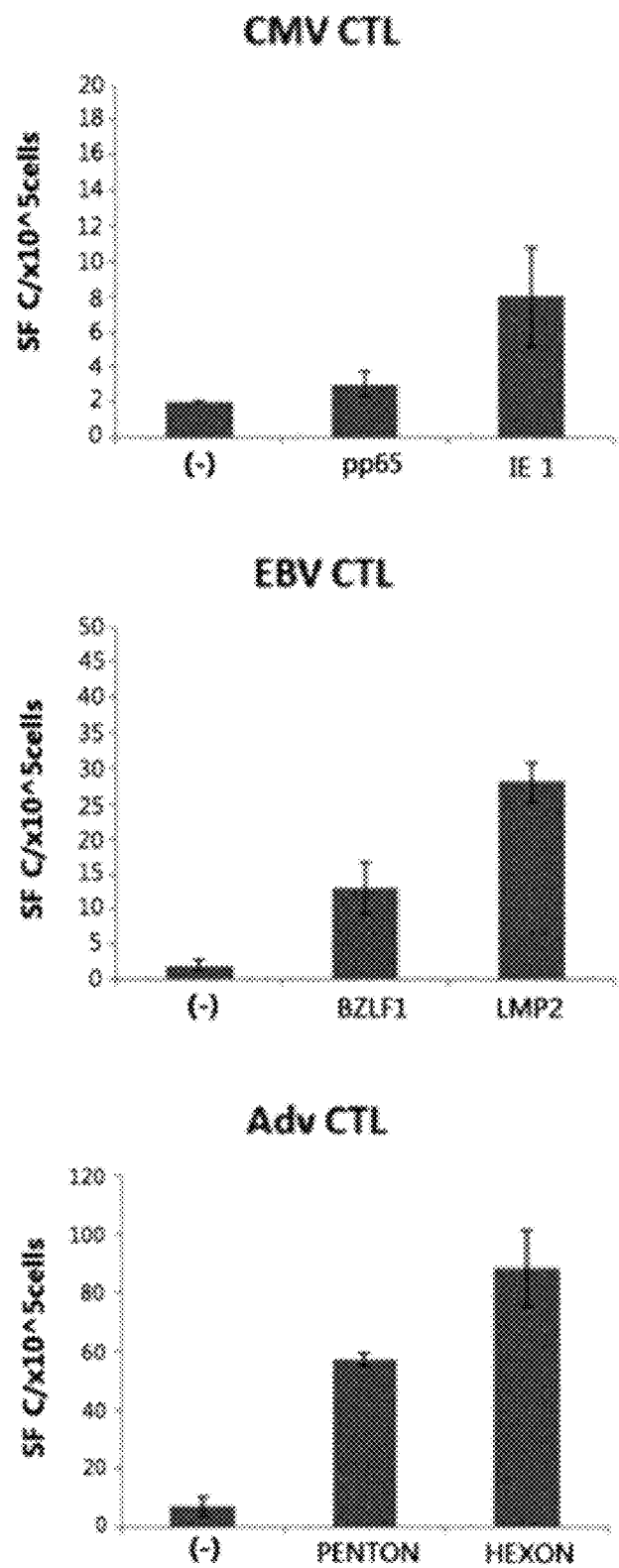

[Fig. 4]
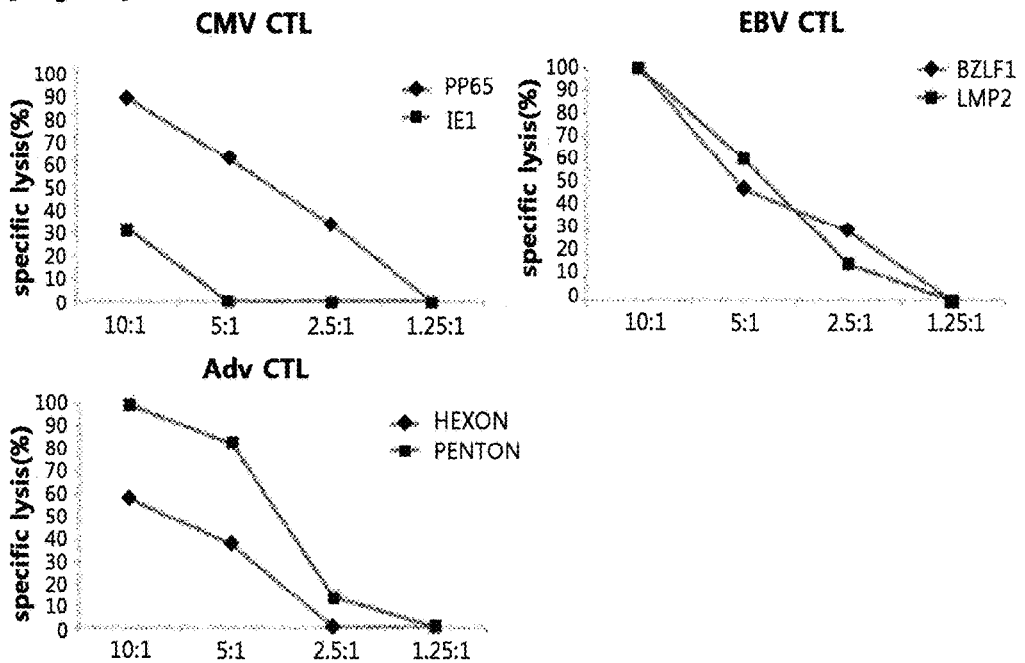
[Fig. 5]
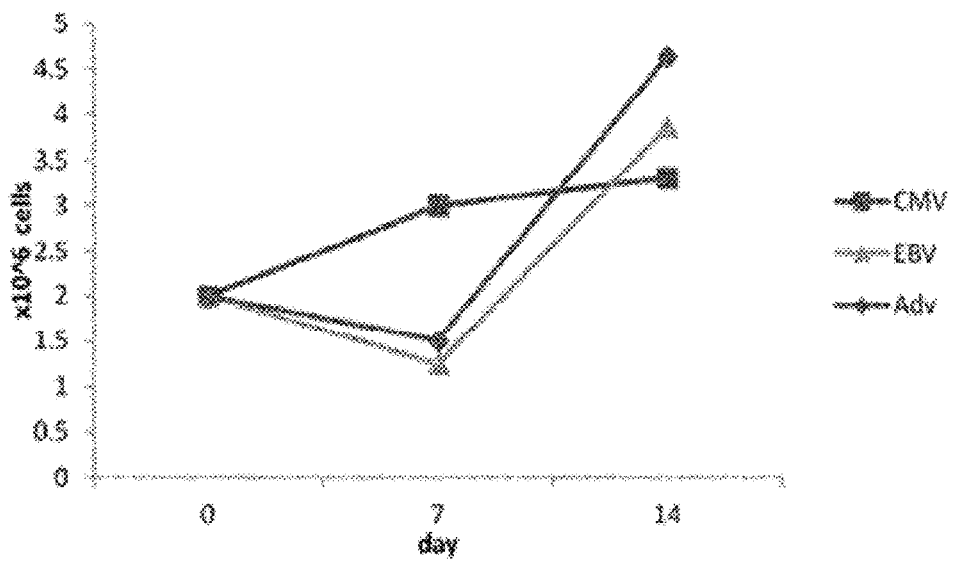

[Fig. 6]
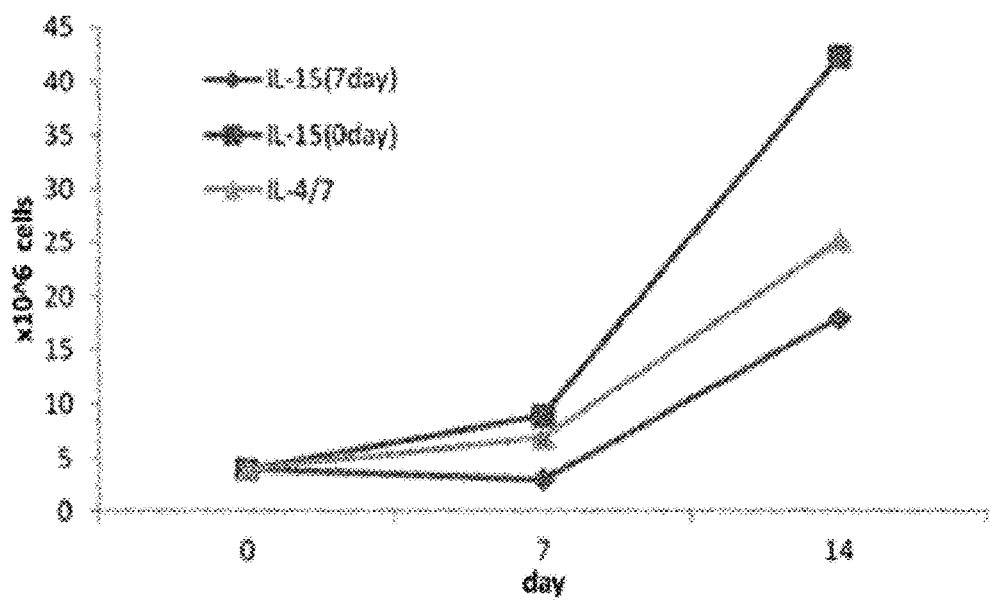
[Fig. 7]
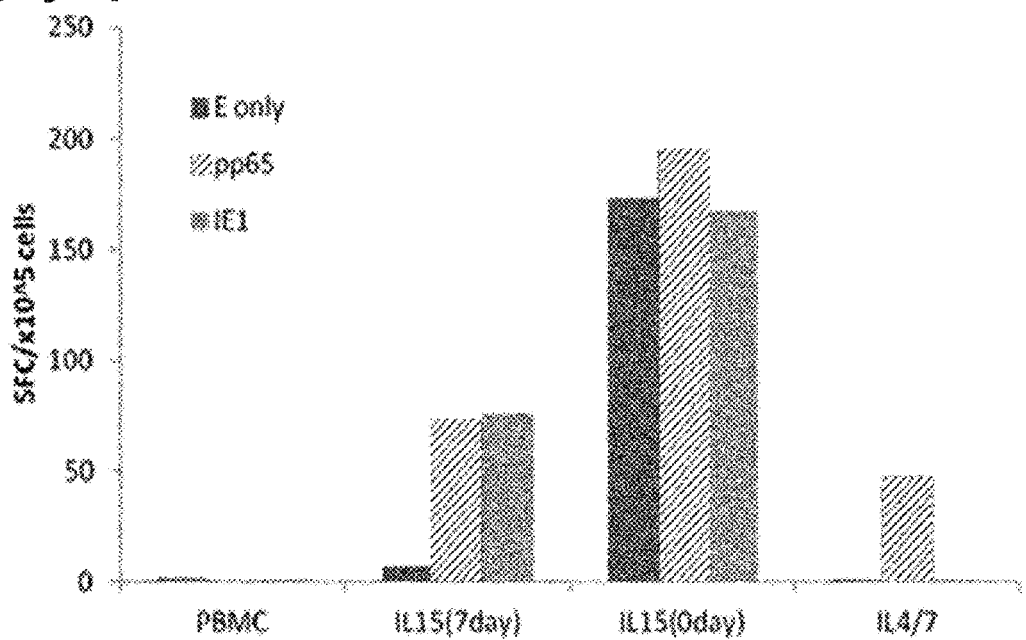

[Fig. 8A]
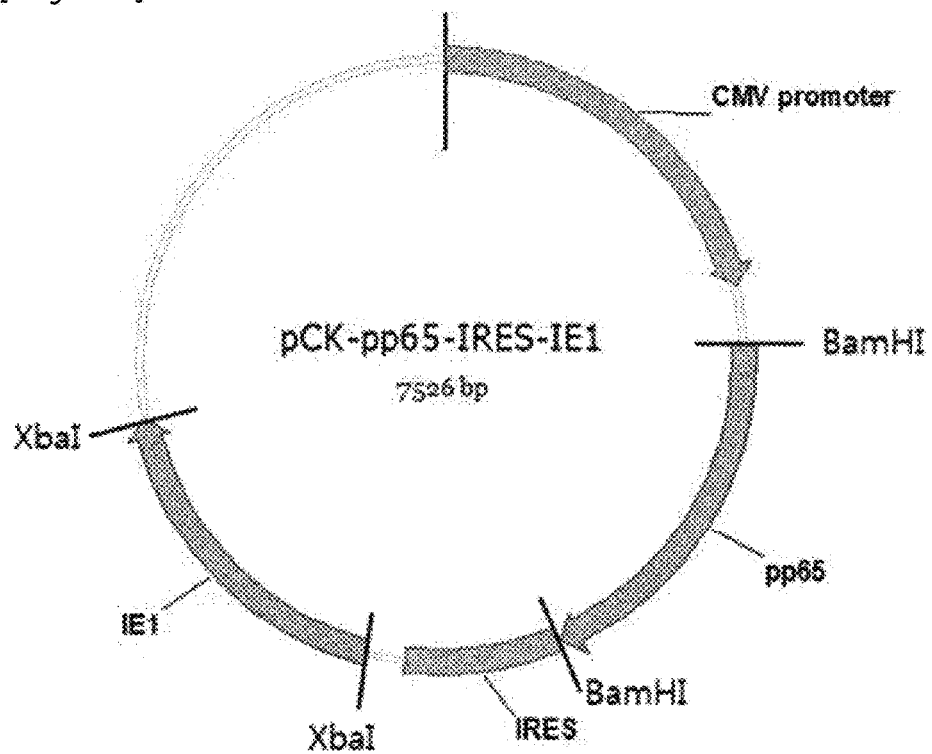
[Fig. 8B]
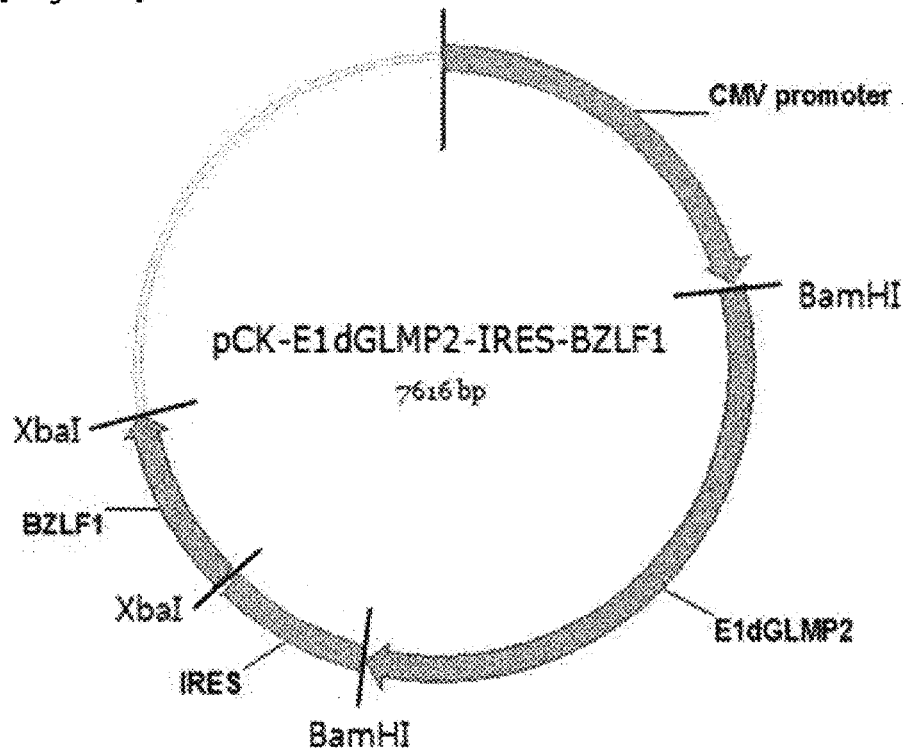

[Fig. 8C]
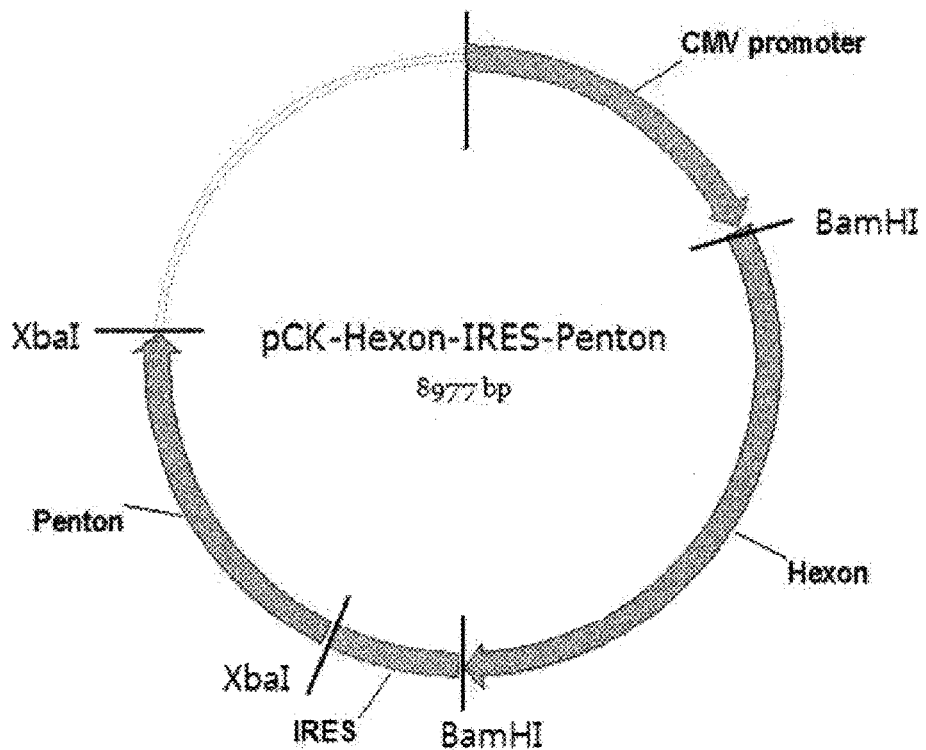
[Fig. 8D]
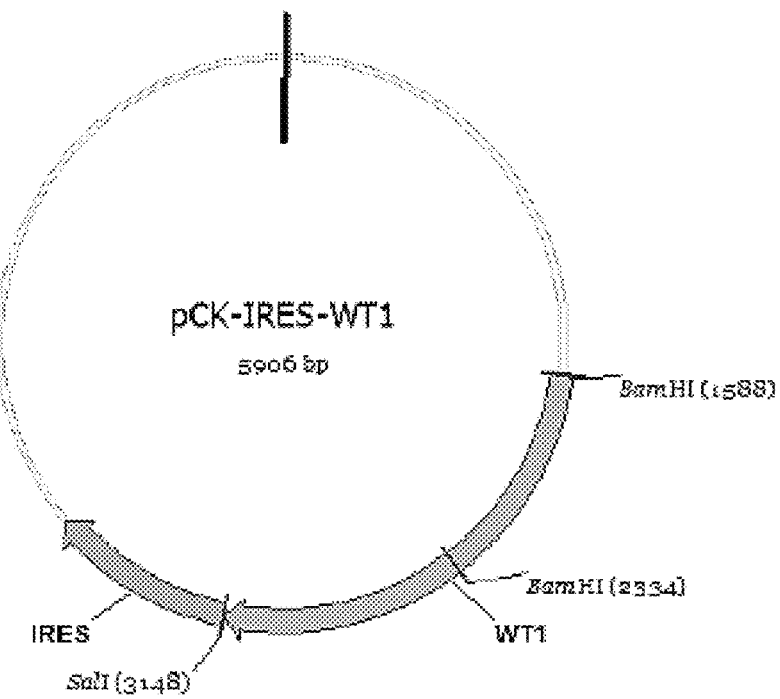

[Fig. 9A]
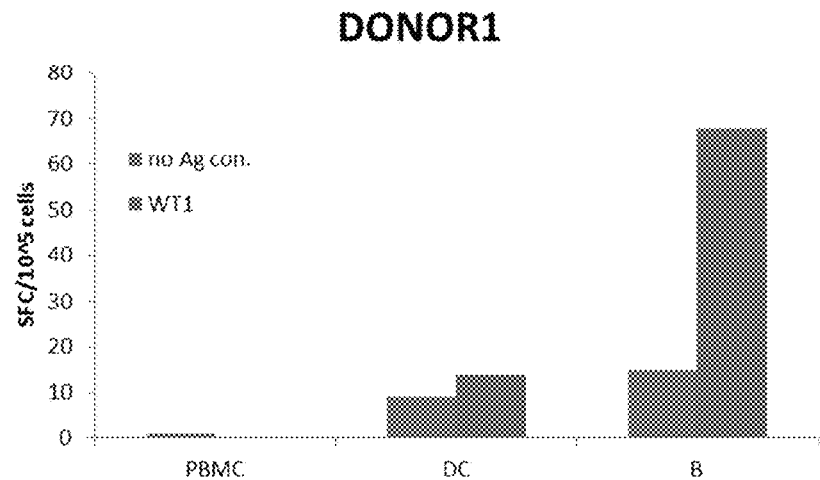
[Fig. 9B]
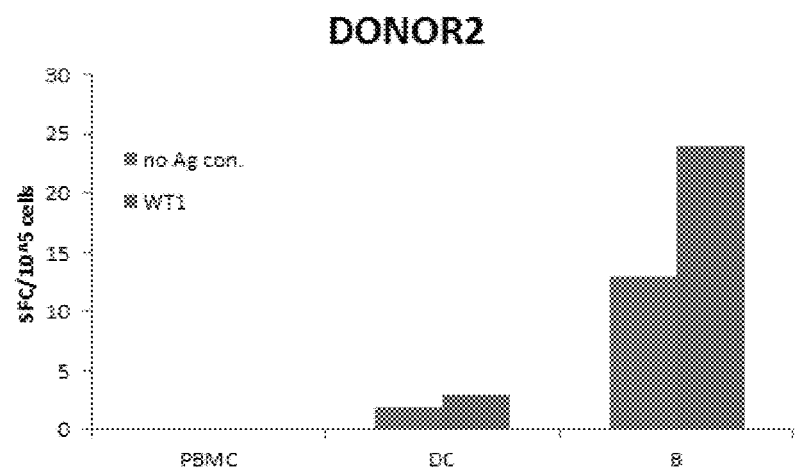
[Fig. 9C]
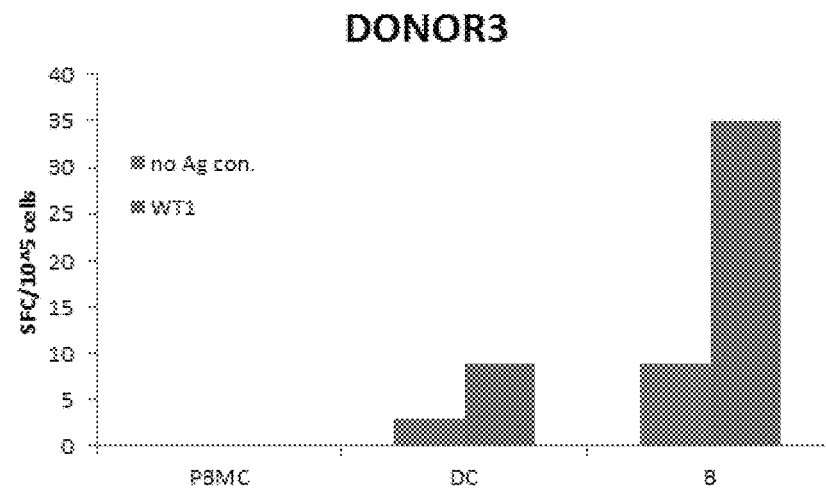

[Fig. 10A]
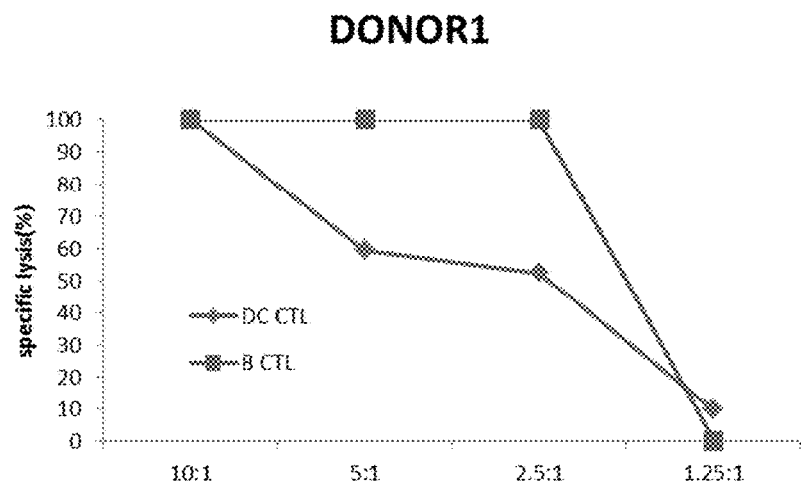
[Fig. 10B]
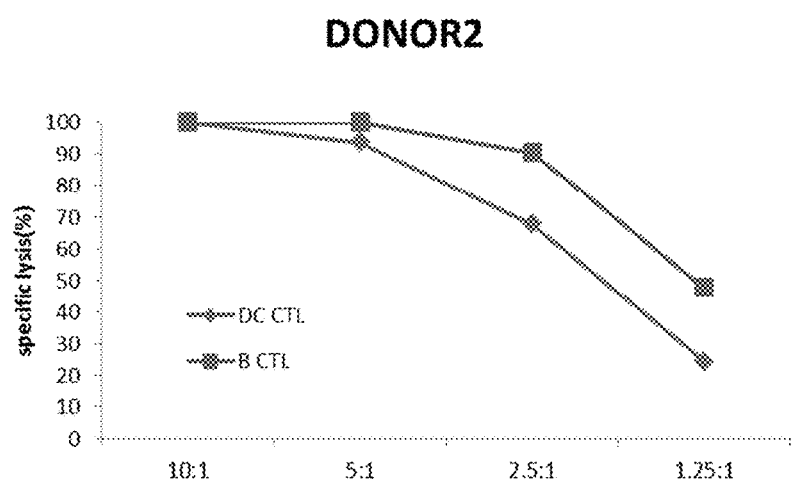
[Fig. 10C]
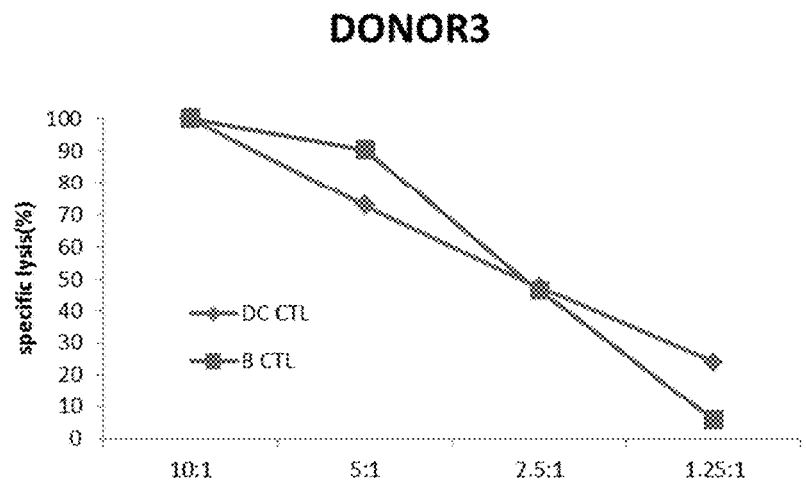

METHOD FOR PREPARING ANTIGEN-SPECIFIC CYTOTOXIC T-CELLS BY USING ACTIVATED B-CELLS AND USE THEREOF

CROSS-REFERENCE TO RELATED APPLICATIONS

The present application is a continuation in part application of International Patent Application No. PCT/KR2015/005075, filed May 21, 2015, and claims the benefit of Korean Patent Application No. 2015-0045476, filed Mar. 31, 2015 in the Korean Intellectual Property Office, the disclosure of which are incorporated herein.

BACKGROUND OF THE INVENTION

Field of the Invention

The present disclosure relates to the field of production of cells used in cellular immunotherapy technology.

Description of the Related Art

Current cell-based therapies are largely divided into two categories: the field of stem cell-based regenerative medicine; and the field of treating cancer and viral infections using immune cells. Among these therapies, cellular immunotherapies using cytotoxic T cells consist mainly of studies based on melanoma models (Rosenberg S A et al., Nat Rev Cancer 8(4):299-308, 2008) and studies based on hematopoietic stem cell transplantation models (Heslop H E et al., New Engl J Med 331:679-680, 1994).

Among them, hematopoietic stem cell transplantation is a therapeutic method that can cure various diseases, but it is not yet a complete therapeutic method. It is known that hematopoietic stem cell transplantation fails due to recurrence of original disease such as leukemia, failure of engraftment, toxicity related to high-dose anticancer therapy, infection caused by graft-versus-host disease (GVHD) and immunosuppression, and the like.

Particularly, infections under immunosuppressive conditions after transplantation pose severe problems, and among them, viral infections often lack propter treatments (Leen A M et al., Br J Hematol 143(2):169-179, 2008; Leen A M et al., Expert Opin Biol Ther 10(3):337-51, 2010). With a recent increase in transplantation from unrelated donors (or cord bloods or haploidentical donors), the use of more potent immunosuppressants has increased, and new immunosuppressants have started to be used in GVHD treatment. Furthermore, with the development of viral infection diagnostic methods, overcoming viral infections is of increasing importance for successful transplantation (Boeckh M et al., Pediatr Transplant 9:48-54, 2005; Bruno B et al., Biol Blood Marrow Transplant 9(5):341-52, 2003; Fischer S A et al., Transplantation 86(10):1327-39, 2008; Leen A M et al., Br J Haematol 128(2):135-44, 2005; Peck A J et al., Blood 110(5):1681-8, 2007; Zerr D M et al., Clin Infect Dis 40(7):932-40, 2005). In addition, the results of unrelated donor transplantation, recently reported in Korea, indicated that death associated with viral infections, particularly EBV or cytomegalovirus (CMV) infections, was the most important cause of transplant failure, and that about 10% of total patients died of such viral infections (Kang H J et al., Ann Hematol 89(10):1035-44, 2010; Kang H J et al., Biol Blood Marrow Transplant 16(11):1582-8 2010).

Multiple-target antiviral cellular immunotherapy, which was recently developed, includes introducing Ad5f35-pp65, which comprises Cytomegalovirus (CMV) antigen pp65 inserted in an adenoviral vector, into donor's monocytes to activate T cells, and then introducing Ad5f35-pp65 again into the Epstein-Barr virus-transformed lymphoblastoid cell line (LCL). This method is effective in activating T cells, but the future application of this method to various viral diseases and a large number of patients will be limited due to a high production cost, a complex production process, a long production period of 10 weeks or more, and the like.

To overcome the complexity and inefficiency of this production method, various efforts have been attempted. Specifically, a plasmid vector was used instead of a difficult-to-handle adenoviral vector, and dendritic cells were used as antigen-presenting cells (APCs). Furthermore, a plasmid was delivered into dendritic cells by nucleofection, and a new combination of cytokines (IL-7: 10 ng/ml, and IL-4: 1,000 U/ml) and a bioreactor were used, thereby increasing the efficiency with which T cells were cultured. The use of this technology simplified the production process and reduced the production cost and the production period (Leen A M et al., Expert Opin Biol Ther 10(3):337-51, 2010).

However, the use of dendritic cells to activate immune cells requires extended amount of time and cost, indicating that the development of a simpler cellular immunotherapy technology is required.

Thus there is a need to develop a more convenient and simpler technology for producing cellular immunotherapeutic agents for cellular immunotherapy of various diseases to be used with treatments involving such as administering cytotoxic T cells activated ex vivo, to human subjects for treatment of various diseases, including viral and other infectious diseases, cancers and immune diseases.

SUMMARY OF THE INVENTION

The present disclosure aims to provide a method for producing antigen-specific cytotoxic T cells, which can be advantageously used for cellular immunotherapy.

In one aspect, the present disclosure provides a method for producing antigen-specific cytotoxic T cells, comprising the steps of: providing human peripheral blood mononuclear cells; separating the peripheral blood mononuclear cells into B cells and mononuclear cells; treating the isolated or separated B cells with any one biological response modifier selected from the group consisting of alpha-galactosylceramide, alpha-glucuronosylceramide, phosphatidylinositol tetramannoside, isoglobotrihexylceramide, ganglioside GD3, phosphatidylcholine, beta-galactosylceramide, lipophosphoglycan, glycoinositol phospholipid, alpha-galactosylceramide analogs, including beta-anomer galactosylceramide and alpha-anomer galactosylceramide, and bacterial lipid antigens, thereby activating the B cells; delivering an antigen-encoding nucleic acid or an antigen peptide into the activated B cells; mixing the antigen-delivered activated B cells with the mononuclear cells separated to produce a first mixture of the cells; subjecting the first mixture of the cells to a first culture/incubation; and after the first incubation, further adding a fresh batch of the antigen-delivered activated B cells to the first mixture of cells to produce a second mixture of the cells and subject the second mixture of the cells to a second incubation, whereby the antigen-specific cytotoxic T cells are produced ex vivo during the first and second incubation steps, particularly the number of the antigen-specific cytotoxic T cells are significantly increased during the second incubation step.

In the method according to the present disclosure, the antigen may be delivered into cells by various methods known in the art. For example, intracellular delivery of the antigen may be performed using the method described in the Example of the present disclosure.

In another aspect, the present disclosure provides a cellular immunotherapeutic agent comprising cells produced according to the method of the present disclosure. In one embodiment, the cellular immunotherapeutic agent according to the present disclosure may be used in combination with other conventional immunotherapeutic agents.

Advantageous Effects

According to the present disclosure, B cells activated by biological response modifiers such as alpha-galactosylceramide are used as antigen-presenting cells for production of antigen-specific cytotoxic T cells instead of dendritic cells (DCs). The use of DCs leads to a higher costs and longer production time. The antigen-specific cytotoxic T cells produced by the present methods can be advantageously used for treatment of infections due to pathogens such as viruses or bacteria, and cancers.

BRIEF DESCRIPTION OF THE DRAWINGS

FIG. 1 schematically shows a T-cell activation method according to one embodiment of the present disclosure, in which B cells activated by alpha-galactosylceramide are used as antigen-presenting cells to produce cytotoxic T cells specific for a viral antigen such as CMV, EBV, Adenovirus or the like, or a tumor antigen.

FIG. 2 schematically shows a method for producing antigen-specific cytotoxic T cells according to one embodiment of the present disclosure, in which the antigen loaded activated B cells are used in two separate steps to produce antigen-specific cytotoxic T cells.

FIGS. 3A and 3B show the results of an ELISpot assay performed to measure IFN-gamma released in an antigen-specific manner from the cytotoxic T cells (CTL) produced according to the present disclosure. Specifically, T cells in FIG. 3A are T cells obtained by co-culture with B cells into which an antigen-encoding nucleic acid was delivered as described in Example 2-1, and T cells in FIG. 3B are T cells obtained by co-culture with B cells into which a peptide acting as an antigen was delivered as described in Example 2-2. SFC means Spot Forming Cells in ELISPOT assay, which are the cells producing IFN-gamma when CTLs encounter antigen expressing target cells which were determined FIG. 4 shows the results of a cytotoxicity assay performed using cytotoxic T cells (CTL) of FIGS. 3A and 3B according to the method of the present disclosure.

FIG. 5 shows the results of measuring the expansion of cytotoxic T cells when the activated B cells were used two times (at day 0 and day 7 during 14 day incubation period) compared to when the activated B cells were used only once (at day 0 during 14 day incubation period).

FIG. 6 shows the results of measuring the expansion/proliferation of T cells depending on the kinds, steps and concentration of cytokine added in the cytotoxic T cell production performed using the activated B cells according to the present disclosure. In FIG. 6, the line connected by diamonds shows the results obtained when IL-15 was added during the second stimulation step; the line connected by square shows the results obtained when IL-15 was added during both first stimulation and second stimulation; and the line connected by triangle shows the results obtained when IL-4 and IL-7 were added during the second stimulation step.

FIG. 7 shows the results of an ELISpot assay performed on the cells treated with the conditions shown in FIG. 6.

FIGS. 8A to 8D are plasmid maps used in the production of antigen-specific cytotoxic T cells according to the present disclosure.

FIGS. 9A to 9C show the results of an ELISpot assay performed to measure IFN-gamma released from the cytotoxic T cells (CTL) from 3 different donors produced in the present disclosure. Specifically, the antigen-specific cytotoxic T cells were obtained by co-culture with the activated B cells loaded with WT1 antigen according to the present methods.

FIGS. 10A to 10C show the results of a cytotoxicity assay performed using the cytotoxic T cells (CTL) of FIGS. 9A to 9C.

DETAILED DESCRIPTION OF THE EMBODIMENTS

The present disclosure is based on the findings that the B cells, which are not known to be adequate to serve as antigen presenting cells because of their low immunity, can be activated (or immunopotentiated) by a biological response modifier such as alpha-galactosylceramide and be used effectively as an antigen-presenting cell to present antigens of interest to immune cells.

The B cells produced by the present methods can thus replace dendritic cells which are time consuming and costly to use, for the production of antigen-specific cytotoxic T cells to present antigens of interest to immune cells in cellular immunotherapy to cope with infections or remove cancer cells.

Therefore, in one aspect, the present disclosure is directed to a method for producing antigen-specific cytotoxic T cells ex vivo using B cells activated by a biological response modifier as an antigen presenting cells.

The method according to the present disclosure comprises the steps of: providing human peripheral blood mononuclear cells; separating the peripheral blood mononuclear cells into B cells and other mononuclear cells other than the B cells; treating the isolated B cells with any one biological response modifier selected from the group consisting of alpha-galactosylceramide, alpha-glucuronosylceramide, phosphatidylinositol tetramannoside, isoglobotrihexylceramide, ganglioside GD3, phosphatidylcholine, beta-galactosylceramide, lipophosphoglycan, glycoinositol phospholipid, alpha-galactosylceramide analogs, including beta-anomer galactosylceramide and alpha-anomer galactosylceramide, and bacterial lipid antigens, to produce activated B cells; delivering or introducing an antigen-encoding nucleic acid or antigen peptide into the activated B cells to produce activated B cells loaded with an antigen of interest; mixing the antigen-loaded activated B cells with the other mononuclear cells separated from the PBMCs to produce a first mixture of the cells; and subjecting the first mixed cells to a first incubation or a first stimulation; and further stimulating the first mixture of cells by adding a fresh antigen-loaded activated B cells to the first mixture to produce a second mixture of the cells and subjecting the second mixture to a second incubation or a second stimulation to produce antigen-specific cytotoxic T cells in vitro or ex vivo.

The peripheral blood mononuclear cells (PBMCs) that are used in the present disclosure include various immune cells present in blood, for example, B cells, T cells, macrophages, natural killer cells, lymphocytes, and monocytes.

In the methods according to the present disclosure, B cells are isolated from PBMCs that are used in the method of the present disclosure. For this, PBMCs are separated into B cells and other mononuclear cells, and the latter cells are referred as responder cells. Methods of isolating PBMCs from the blood and separating B cells and other mononuclear cells other than the B cells from PBMCs are known in the art. For example, these methods may be performed using the methods described in the Examples of the present disclosure.

In the methods according to the present disclosure, human peripheral blood mononuclear cells of autologous or allogeneic origin may be used. In one embodiment, blood collected from a subject may be treated in vitro according to the present methods as disclosed to obtain the cells of interest, and the cells may be injected into the same subject.

In the method according to the present disclosure, B cells are activated or immunopotentiated using a biological response modifier. The term "biological response modifier" in the present disclosure refers to a material able to immunopotentiate B cells particularly through CD1d receptor protein present on the membrane of B cell.

The ligands which bind or are recognized by CD1d receptor protein include various non-peptide materials such as lipids, glycolipids and the like. Thus, various materials which function as a ligand of CD1 receptor may be used as a biological response modifier of the present disclosure to activate the B cells including but not limited to materials selected from the group consisting of alpha-galactosylceramide, alpha-glucuronosylceramide, phosphatidylinositol tetramannoside, isoglobotrihexylceramide, ganglioside GD3, phosphatidylcholine, beta-galactosylceramide, lipophosphoglycan, glycoinositol phospholipid, alpha-galactosylceramide analogs, including beta-anomer galactosylceramide and alpha-anomer galactosylceramide to produce activated B cells. These materials are all known as a ligand for CD1d (Brutkiewicz, CD1d Ligands: The Good, the Bad, and the Ugly, J Immunol 2006; 177:769-775).

In the present disclosure, the activated B cells are loaded with a particular antigen of interest.

The antigens or ligands which may be loaded or expressed in the activated B cells of the present disclosure are not particularly limited as long as it can produce cytotoxic T cell specific for the antigen or ligands loaded and may be classified in terms of chemical properties. According to this classification, the antigens include peptides, lipopolysaccharides, polysaccharides, glycoproteins or polynucleotides.

In other embodiment, the antigens that are expressed in the present B cells may be classified in functional terms. According to this classification, the antigens include antigens derived from pathogens, including pathogenic bacteria, viruses and parasites, or cancer-related antigens.

In one particular embodiment, a viral antigen is used. The viral antigen is selected from the group consisting of Epstein-Barr virus (EBV) antigen (see E1dGALMP2 Mol Ther. 2013 November; 21(11):2113-21; immediate early protein BZLF1), cytomegalovirus (CMV) antigen (pp65, IE1), Adenovirus (Adv) antigen (HEXON, PENTON), influenza virus antigen, human papilloma virus (HPV) antigen (glycoprotein), vesicular stomatitis virus antigen (vesicular stomatitis virus glycoprotein), hepatitis A (HAV), B (HBV), C (HCV), D (HDV) and G (HGV) antigens (core antigen and surface antigens), respiratory synctytial virus (RSV) antigen, herpes simplex virus antigen, human immunodeficiency virus (HIV) antigen (GP-120, GP-160, p18, Tat, Gag, Pol, Env), and combinations thereof. Also included are full or partial length of the antigens as described above.

In the method according to the present disclosure, the antigen is provided in a form of a nucleic acid encoding a full or partial length of an antigen of interest, or form of a peptide or protein of partial or full length for intracellular delivery. In one embodiment, a vector that is used for delivery of a nucleic acid may be a plasmid vector expressing an antigen of interest in full or partial length, and may be delivered to the nucleus of B cells by a nucleofection as described in the present disclosure. The vector which may be used for the present methods are known in the art and may be selected by a person in the art without difficulty in reference to the Examples of the present disclosure.

In one embodiment, the antigens that are used in the method of the present disclosure are viral antigens EBV, CMV and Adv antigens, which may be delivered by a vector pCK-pp65-IRES-IE1, pCK-E1dGALMP2-IRES-BZLF1 and pCK-HEXON-IRES-PENTON, respectively, as shown in FIGS. 8A to 8C and the methods described in the Examples of the present disclosure.

In another embodiment, the tumor antigens are used which include, but are not limited to, carcinogenic proteins, including WT1, MAGE1, AFP, CEA or tyrosinase, or tumor-specific antigens, including telomerase, BCR-ABL or RHAMM-R3. In addition, an antigenic peptide or the like may be used as the antigen. In one embodiment WT1 antigen is introduced to the activated B cells using as a vector for example pCK-WT1 shown in FIG. 8D.

It is found in the present method that the number of antigen-specific cytotoxic T cells is significantly increased when the activated B cells loaded antigen and responder cells are incubated in two independent steps and further adding a fresh activated B cells loaded antigen at a second step.

In the method according to the present disclosure, nucleofected B cells and mononuclear cells other than the B cells separated from PBMC are cultured or incubated together to produce cytotoxic T cells specific for the antigen of interest expressed in the B cells. In one embodiment, the nucleofected activated B cells and the responder cells (mononuclear cells other than the B cells) are used in a cell number ratio of about 1:20 to 1:1, particularly 1:10.

Further in the method according to the present disclosure, a cytokine may be added during the first and/or second incubation or stimulation step, particularly at/during the second incubation step. In one embodiment, the cytokines are added at the start of a second incubation step and/or further added when the cell medium is changed.

The kinds of cytokines that may be used in the present disclosure are not particularly limited, and includes IL-15, IL-2, IL-4, IL-7 or IL-9. The cytokine may be used at a concentration of about 10-100 ng/ml. The cytokines may be added at the start of a second incubation step and further added when the cell medium is changed.

According to the method of the present disclosure, highly effective antigen-specific cytotoxic T cells can be produced in a more rapid and cost-effective manner by using the B cells activated by, for example, alpha-galactosylceramide, as antigen-presenting cells for production of antigen-specific cytotoxic T cells, instead of dendritic cells (DCs). A comparison between the method of the present disclosure and conventional methods is as follows.

| Methods | Reference | Production process | Production time | Production cost |
|---|---|---|---|---|
| Traditional method | Amrolia P J. 2006 | Complex | >10 weeks | Very high |
| DC-based method | Leen A M. 2010 | Relatively simple | 2-3 weeks | High |
| The present Method based on the activated B cells | The present disclosure | Simple | 1-2 weeks | Low |

Currently, for treatment of viral infections, administration of antiviral agents is used as standard therapy. However, there are many problems in that a therapeutic drug against a particular virus is not present in many cases, and even if the therapeutic drug is present, it is highly costly, is toxic by itself, can be temporarily effective, and cannot achieve treatment due to drug resistance. In comparison with this, treatment with the antigen-specific cytotoxic T cells according to the present disclosure enables the patient to restore antiviral immunity against a viral infection that is a fundamental etiological cause. In one embodiment, blood collected from a subject may be processed in vitro according to the method described in the present disclosure to obtain cells, and the cells may be injected into the same subject.

Therefore, in another aspect, the present disclosure is also directed to a cellular immunotherapeutic agent, comprising antigen-specific cytotoxic T cells induced by B cells which have a biological response modifier loaded thereon and which express a pathogenic bacterial antigen, a viral antigen or a cancer-related antigen.

As used herein, the term "cell therapeutic agent" or "cell immunotherapeutic agent" refers to a pharmaceutical product which is used for the purposes of treatment, diagnosis and prevention to restore the structure and function of cells and which is obtained through a series of actions, including growing and screening living autologous or allogeneic cells ex vivo or changing the biological characteristics of cells by any other methods (Regulations for the Approval and Examination of Biological Agents (Korea Food and Drug Administration Notification)).

In one embodiment, the cellular immunotherapeutic agent according to the present disclosure may further comprise other immunotherapeutic agents.

The cellular therapeutic agent according to the present disclosure includes autologous cell therapeutic agents or allogeneic cell therapeutic agents.

The cellular therapeutic agent according to the present disclosure may be produced by separating cells, subjecting the isolated cells to necessary operations using the method described in the present disclosure to produce cytotoxic T cells ex vivo, and the produced T cells may be administered. For example, antiviral immune cells may be produced ex vivo and administered. For example, the method described in Lindvall et al. 1989, Arch. Neurol. 46: 615-31 or Douglas Kondziolka, Pittsburgh, 1998, may be used.

In one embodiment, treatment with the antigen-specific cytotoxic T cells according to the present disclosure enables the patient to restore antiviral immunity against a viral infection that is a fundamental etiological cause. In particular, the antigen-specific cytotoxic T cells according to the present disclosure may be used for treatment of infections or immunosuppressed viral infections after organ transplantation.

The cellular therapeutic agent according to the present disclosure or a pharmaceutical composition comprising the cells according to the present disclosure may be administered by any general route, as long as it can reach a target tissue. Specifically, the pharmaceutical composition may be administered parenterally, for example, intraperitoneally, intravenously, intramuscularly, subcutaneously or intradermally, but is not limited thereto.

The therapeutic agent or composition according to the present disclosure may be formulated into a suitable form using a pharmaceutically acceptable carrier that is generally used. The pharmaceutically acceptable carriers include, for example, carriers for parenteral administration, such as water, suitable oil, saline solution, aqueous glucose and glycol, and may further comprise stabilizers and preservatives. Suitable stabilizers include antioxidants such as sodium hydrogen sulfite, sodium sulfite or ascorbic acid. Suitable preservatives include benzalkonium chloride, methyl- or propyl-paraben and chlorobutanol. In addition, the cell therapeutic composition according to the present invention may, if necessary, contain a suspending agent, a dissolution aid, a stabilizer, an isotonic agent, a preservative, an adsorption preventing agent, a surfactant, a diluent, an excipient, a pH adjusting agent, a pain relieving agent, a buffer, an antioxidant or the like depending on the administration method or formulation thereof. Pharmaceutically acceptable carriers and formulations suitable for use in the present invention, including those mentioned above, are described in detail in Remington's Pharmaceutical Sciences (latest edition).

The cell therapeutic composition according to the present invention may be formulated using a pharmaceutically acceptable carrier and/or excipient according to a method that may be easily carried out by those skilled in the field to which the present invention pertains. The formulated composition may be prepared as a unit dosage form or may be packaged in a multiple-dose container.

Furthermore, the composition may also be administered by any device capable of delivering the cellular therapeutic agent to target cells. The cell therapeutic composition according to the present invention may contain a therapeutically effective amount of the cellular therapeutic agent for disease treatment. The term "therapeutically effective amount" means the amount of active ingredient or pharmaceutical composition required to elicit a biological or medical response in tissues, animals or humans, which is thought by researchers, veterinaries, physicians or other clinicians. The term includes an amount that is enough to produce alleviation of a disease or disorder to be treated. It will be obvious to those skilled in the art that the therapeutically effective amount of the cellular therapeutic agent comprised in the composition of the present invention may vary depending on a desired effect.

Accordingly, the optimum amount of the cellular therapeutic agent in the composition can be easily determined by those skilled in the art, and may vary depending on various factors, including the kind of disease, the severity of the disease, the contents of other components in the composition, the kind of formulation, the patient's age, body weight, general health condition, sex and diet, the time of administration, the route of administration, the secretion rate of the composition, the treatment period, and drugs used concurrently with the composition. In one embodiment of the present disclosure, the cellular therapeutic agent is administered into a blood vessel by injection.

Considering all the above factors, it is important to determine the least amount possible with which the maximum effect can be achieved without a side effect. The prescribed dosage may vary depending on factors such as the formulation method, the mode of administration, the patient's agent, body weight, sex, disease condition, diet, the administration time, the route of administration, excretion rate and responsiveness, and any person skilled in the art can suitably determine the dose in view of such factors. The frequency of administration may be once, or twice or more within the range of clinically acceptable side effects, and the site of administration may be one, two or more sites. For animals other than humans, a dosage that is the same as that of per kg in a human, or a dosage that is determined by, for example, conversion based on the volume ratio (e.g., average value) of ischemic organs (e.g., heart) of the target animal and a human, may be administered.

Examples of animals to be treated according to the present invention include humans and other mammals of interest. Specifically, examples of the animals include humans, monkeys, mice, rats, rabbits, sheep, cows, dogs, horses, pigs and the like.

Hereinafter, examples will be presented to help understand the present invention. However, the following examples are merely provided to facilitate understanding of the present invention, and the scope of the present invention is not limited by these examples.

EXAMPLES

Example 1

Isolation of B Cells from Peripheral Blood Mononuclear Cells and Activation of the B Cells Human peripheral blood samples were collected from healthy volunteers under informed consent. Then, peripheral blood mononuclear cells (PBMCs) were isolated from the peripheral blood by Ficoll-Paque™ plus (GE Healthcare) density gradient centrifugation according to the manufacturer's instructions. This study was approved by the Institutional Review Board for Human Research of Seoul National University (IRB No. C-1207-087-418).

After the density gradient centrifugation, using a B cell isolation kit II (Miltenyi Biotec, Bergisch Gladbach, Germany) according to the manufacturer's instructions, B cells were isolated from the PBMCs through negative selection using the anti-CD2, anti-CD14, anti-CD16, anti-CD36, anti-CD43 and anti-CD235a bound to magnetic microbeads. The purity of the isolated cells was analyzed using flow cytometry (FACSCanto™II, BD bioscience) and determined to be 95% or more. The isolated cells were treated with a-GalCer in 10% FBS-containing RPMI or frozen and stored until use.

The isolated B cells were activated in the following manner and nucleofected with an antigen-encoding plasmid to load with a particular antigen, and then used as stimulator cells. Other mononuclear cells remaining after isolation of the B cells were used as responder cells. The B cells isolated as described above were activated by treating $1 \times 10^6$ cells/ml with 1 µg/ml of alpha-galactosylceramide in 10% RPMI medium at 37° C. for about 16 hours.

Example 2

Antigen Loading 2-1: Construction of Antigen-Encoding Plasmid and Loading by Nucleofection The antigenic site of each of pCK-IE1-IRES-pp65 (IE1, pp65), pCK-E1dGALMP2-IRES-BZLF1 (E1dGALMP2, BZLF1) and pCK-HEXON-IRES-PENTON (HEXON, PENTON), which are plasmids encoding EBV, CMV and Adv antigens, respectively, was cloned into a pCK-IRES (ViroMed, Korea) vector, thereby constructing the following vectors, each encoding two of EBV, CMV and Adv antigens: pCK-IE1-IRES-pp65, pCK-E1dGALMP2-IRES-BZLF1 and pCK-HEXON-IRES-PENTON. WT1 (Wilms Tumor) gene (OriGene Inc. USA) was cloned into pCK-IRES (Viromed, Korea) vector to produce pCK-WT1.

The plasmids constructed as described above were then introduced into the activated B cells (prepared in Example 1) to load activated B cells with antigen using an AMAXA® Nucleofection® system (Lonza, USA) according to the manufacturer's instructions. Briefly, $1-5 \times 10^6$ activated B cells were nucleofected with 1-5 µg of plasmid DNA, and then incubated in a humidified 5% $CO_2$ incubator at 37° C. for 12-18 hours.

2-2: Delivery of Antigen Polypeptide

Pepmixes (JPT, Germany), which are peptide libraries of the CMV antigen PP65, the 1 µg and EBV antigen LMP2, BZLF1, the Adenovirus antigen HEXON and PENTON, and cancer antigen WT1 was dissolved in PBS and used in an amount of 1 µg g/test. The activated B cells and 1 µg of the pepmix prepared as described above were mixed together and incubated in a humidified 5% $CO_2$ incubator at 37° C. for 1-2 hours. After the first incubation, the B cells were further mixed and incubated with the other mononuclear cells remained from the B cell isolation in the same manner as the plasmid-nucleofected B cells.

Example 3

Production of Cytotoxic T Cells

The mononuclear cells other than the B cells separated from PMBC in Example 1 were used as responder cells, and the nucleofected B cells and the antigen polypeptide-delivered B cells as described in Examples 2-1 and 2-2 were used as stimulator cells. The responder cells and the stimulator cells were co-cultured in RPMI 1640 medium containing 45% Click's medium (Irvine Scientific, CA, USA), 2 mmol/L Glutamax™-I and 10% FBS. At day 7 of culture, the cells were harvested and re-stimulated with stimulator cells. From day 7 of culture at the re-stimulation step, 50 ng/ml of IL-15 was added. After the re-stimulation, antigen-specific immune responses were assayed.

Specifically, for the first stimulation, the responder cells and the nucleofected B cells were mixed at a concentration ratio of 10:1 and co-cultured for 7 days without medium replacement. At day 7, the cells were harvested, mixed with fresh batch of nucleofected activated B cells at a ratio of 10:1, and cultured (second incubation). IL-15 was added at the concentration of 50 ng/ml at the start of the second culture and when the medium is replaced as described below. The medium was replaced at a level of 30-40% with 2-3-day intervals.

The induced cytotoxic T cells were then analyzed by flow cytometry. For the flow cytometry assay, the cells were harvested, washed, resuspended in DPBS, and then incubated with various fluorescence protein-coupled antibodies (CD3, CD4, CD8, CD56, CD45RA and CD62L) (BD Pharmingen) in a refrigerator at 4° C. for 15 minutes in a dark room. Thereafter, the cells were washed, resuspended, and then analyzed by FACSCanto™ II (BD bioscience). The results of the analysis indicated that CD4 and CD8 cells had a T-cell population of 80% or more, and NKT cells had a T-cell population of less than 5%. In addition, CD45RA+ CD62L+ indicating naive cells was reduced, CD45RA- CD62L+ indicating central memory cells and CD45RA- CD62L-indicating effector memory cells increased.

Example 4

Enzyme-Linked Immunospot (ELISpot) Assay

The cytotoxic T cells produced in Example 3 were assayed for interferon-gamma (IFN-γ) release using an ELISpot assay kit (BD bioscience) according to the manufacturer's instructions. In the assay, mononuclear cells from the same donor were used as antigen-presenting cells, and pepmixes (JPT Technologies, Germany), which are peptide libraries (15-mers with 11 amino acid overlapping), were used for virus antigens; and pCK-WT1 nucleofaction was used for tumor antigen. The results of the assay are shown in FIGS. 3A and 3B and 9A, 9B and 9C. As shown therein, it was found that the cytotoxic T cells released interferon-gamma in a manner specific for each viral antigen and tumor antigen.

Example 5

Cytotoxicity Assay

In this Example, autologous mononuclear cells were stimulated with the B cells (treated with each antigen) prepared in Example 2, and then treated with the antigen as described in Example 4. The autologous mononuclear cells were used as target cells. Antigen lysis was measured using the CytoTox96® Non-Radioactive Cytotoxicity Assay (Promega, USA) kit according to the manufacturer's instructions. The kit measures the stable cytosolic enzyme LDH (Lactate Dehydrogenase) that is released upon cell lysis. Cytotoxicity was calculated as the percentage of specific lysis using the following equation:

Specific lysis percentage=[(Experimental release—Effector Spontaneous release—Target Spontaneous release)/(Target Maximum release−Target Spontaneous release)]×100. The results are shown in FIGS. 4, 5 and 10A, 10B and 10C. As shown therein, the target cells with each of CMV, EBV and Adv as viral antigens and with WT1 as a tumor antigen were effectively killed by the cytotoxic T cells induced for 2 weeks according to the present invention.

Example 6

Results of T-Cell Expansion Depending on the Number of Stimulations and Cytokine Treatment In this Example, the mononuclear cells remaining after the isolation of B-cell as described in Example 1 were used as responder cells, and the nucleofected B cells as described in Example 2 were used as stimulator cells. The responder cells and the stimulator cells were co-cultured in RPMI 1640 medium containing 45% Click's medium (Irvine Scientific, CA, USA), 2 mmol/L Glutamax™-I and 10% FBS. At day 7 of culture, the cells were harvested and restimulated. The cells were counted after the second stimulation. IL-15 (7 day) group of cells were incubated in the presence of IL-15 at the concentration of 50 ng/ml from day 7 (the day of second stimulation), IL-15 (0 day) group of cells were incubated in the presence of IL-15 at the concentration of 50 ng/ml from the first day of first stimulation. For the IL-4/7 group of cells, 1000 U/ml of IL-4 and 10 ng/ml of IL-7 were simultaneously added from day 7 (the day of second stimulation).

Specifically, for the first stimulation, the responder cells remaining after B-cell isolation and the nucleofected B-cells (antigen loaded activated cells) were mixed at a concentration ratio (cell number) of 10:1 and co-cultured for 7 days without medium replacement. At day 7, the cells were harvested, mixed with a second batch fresh nucleofected activated B cells at a ratio of 10:1, and then subject to a second culture. During the second culture, cytokine was added at the same concentration as described above. Next, the medium was replaced at a level of 30-40% every 2-3-days. The results are shown in FIG. 6.

Next, from the induced cytotoxic T cells shown in FIG. 6, cells that release interferon-gamma (IFN-γ) were assayed using an ELISpot assay kit (BD Bioscience) according to the manufacturer's instruction. In the assay, mononuclear cells from the same donor were used as antigen-presenting cells, and pepmixes (JPT Technologies, Berlin, Germany), which are peptide libraries (15-mers with 11 amino acid overlapping), were used as antigens. The results are shown in FIG. 7. As shown therein, the cytotoxic T cells released interferon-gamma in a manner specific for each viral antigen. The results are shown in FIG. 7.

As shown in FIGS. 6 and 7, FIG. 6 indicates that the expansion of the T cells significantly increased when the cells were stimulated twice with the activated B cells compared to when the cells were stimulated once. After 7 days of stimulation, when the cells were harvested and counted, it is shown that the number of the cells was reduced. It is thought to be that T cells not specific to antigen or mononuclear cells other than T cells were killed during the stimulation period.

In addition, from the results shown in FIG. 6, the cell expansion was the best in the group to which IL-15 was added during the first stimulation and second stimulation. However, as shown in FIG. 7, the results of the ELISpot and cell death assays indicated that the group to which IL-15 was added during second stimulation showed the best results. This is believed to be that the number of antigen-specific T cells efficiently increased when they were treated with the cytokine at day 7 (the day of second stimulation). Furthermore, the cell population was analyzed by FACS. As a result, it was shown that when IL-15 was added during the first stimulation and second stimulation, NK cells increased. This is believed to be that the non-antigen-specific cells were expanded by the cytokine (data not shown).

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

Unless defined or interpreted otherwise, all technical and scientific terms and any acronyms used herein have the same meanings as commonly understood by one of ordinary skill in the art in the field of the invention. The contents of all publications disclosed as references herein are incorporated herein by reference.

What is claimed is:

1. A method of producing antigen-specific cytotoxic T cells, comprising the steps of:
   providing human peripheral blood mononuclear cells;
   separating the peripheral blood mononuclear cells into B cells and other mononuclear cells;
   treating the B cells with any one of biological response modifiers selected from the group consisting of alpha-galactosylceramide, alpha-glucuronosylceramide, phosphatidylinositol tetramannoside, isoglobotrihexylceramide, ganglioside GD3, phosphatidylcholine, beta-galactosylceramide, lipophosphoglycan, glycoinositol phospholipid, alpha-galactosylceramide analogs, including beta-anomer galactosylceramide and alpha-anomer galactosylceramide to produce activated B cells;

introducing into the activated B cells an antigen polypeptide or a DNA encoding an antigen to produce activated B cells loaded with an antigen;

mixing a first batch of the antigen-loaded activated B cells and the other mononuclear cells separated from the peripheral blood mononuclear cells to produce a first mixture of the cells;

subjecting the first mixture of the cells to a first incubation;

adding a second batch of the antigen-loaded activated B cells to the first mixture of the cells after the first incubation to produce a second mixture; and subjecting the second mixture to a second incubation, wherein a cytokine is added only during the second incubation step and wherein the antigen-specific cytotoxic T cells are generated during the first and the second incubation steps.

2. The method of claim 1, wherein the cytokine is at least one of IL-15, IL-2, IL-4, IL-7 and IL-9.

3. The method of claim 2, wherein the cytokine is added at a concentration of 10-100 ng/ml.

4. The method of claim 1, wherein the antigen is an antigen from a pathogen including a virus, a pathogenic bacterium or a parasite, or a tumor antigen.

5. The method of claim 4, wherein the antigen from the virus is selected from the group consisting of an Epstein-Barr virus (EBV) antigen including E1dGALMP2 or BZLF1, a cytomegalovirus (CMV) antigen including pp65 or 1E1, an Adenovirus (Adv) antigen including HEXON or PENTON, an influenza virus antigen, a human papilloma virus (HPV) antigen, a vesicular stomatitis virus antigen, a hepatitis A, B, C, D or G virus antigen including a core antigen or a surface antigen, a respiratory synctytial virus antigen, a herpes simplex virus antigen, a human immunodeficiency virus antigen including GP-120, GP-160, p18, Tat, Gag, Pol or Env, and combinations thereof.

6. The method of claim 5, wherein the antigen is an EBV, CMV or Adv antigen.

7. The method of claim 6, wherein the EBV, CMV and Adv antigens are encoded by pCK-IE1-IRES-pp65, pCK-E1dGALMP2-IRES-BZLF1 and pCK-HEXON-IRES-PENTON plasmid vectors, respectively as shown in FIGS. 8A, 8B and 8C, respectively.

8. The method of claim 1, wherein the antigen is a tumor antigen.

9. The method of claim 8, wherein the tumor antigen is selected from tumor specific proteins including MAGE1 (Melanoma Associated Antigen), AFP (Alpha Feto Protein) CEA (Carcinoembryonic Antige) or tyrosinase, tumor-specific antigens including telomerase, BCR-ABL (Abelson-Break point cluster) or RHAMM-R3 (receptor for hyaluronic acid-mediated motility), or WT1 (Wilms Tumor protein) and any mutant forms thereof.

10. The method of claim 9, wherein the tumor antigen is WT1.

11. The method of claim 10, wherein the WT1 is encoded by pCK-WT1 shown in FIG. 8D.

12. The method of claim 1, wherein the antigen-loaded activated B cells and the other mononuclear cells separated from the peripheral blood mononuclear cells at the first mixture or at the second mixture are present at a ratio of 1:20 to 1:1 in cell number.

13. The method of claim 1, wherein the human peripheral blood mononuclear cells are autologous or allogeneic.

14. A cell immunotherapeutic agent comprising the cells produced according to claim 1.

* * * * *